US005805714A

United States Patent [19]

Kasama et al.

[11] Patent Number: 5,805,714

[45] **Date of Patent: *Sep. 8, 1998**

[54] NOISE SUPPRESSOR IN IMAGE FORMING APPARATUS AND NOISE SUPPRESSING METHOD

[75] Inventors: Minoru Kasama; Koji Udagawa; Masahiro Mori, all of Nakai-machi, Japan

[73] Assignee: Fuji Xerox Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 731,753

[22] Filed: Oct. 18, 1996

[30] Foreign Application Priority Data

Nov. 13, 1995 [JP] Japan .................................... 7-317063

[51] Int. Cl.$^{6}$ ............................ A61F 11/06; H03B 29/00

[52] U.S. Cl. ......................................... 381/71.8; 381/71.1

[58] Field of Search ....................... 381/71, 94; 358/471; 355/200, 202

[56] References Cited

U.S. PATENT DOCUMENTS

| | | | |
|---|---|---|---|
| 5,111,242 | 5/1992 | Tanimoto et al. | 355/200 |
| 5,289,147 | 2/1994 | Koike et al. | 381/71 |
| 5,406,383 | 4/1995 | Tanaka | 358/401 |
| 5,418,629 | 5/1995 | Miura | 358/471 |
| 5,427,102 | 6/1995 | Shimode et al. | 381/71 |
| 5,590,206 | 12/1996 | An et al. | 381/71 |

FOREIGN PATENT DOCUMENTS

| | | |
|---|---|---|
| A-2-97877 | 4/1990 | Japan . |
| A-5-142887 | 6/1993 | Japan . |
| A-6-8581 | 1/1994 | Japan . |

*Primary Examiner*—Curtis A. Kuntz

*Assistant Examiner*—Ping W. Lee

*Attorney, Agent, or Firm*—Oliff & Berridge, PLC

[57] ABSTRACT

A noise suppressor in an image forming apparatus suppresses noise from a drive mechanism during operation. An operation start signal of the drive mechanism is detected. A previously stored secondary sound having a reversed waveform to the waveform of the noise is generated at a noise suppressing position based on the drive operation start signal.

14 Claims, 10 Drawing Sheets

50 51 52

| DESIGNATED FUNCTION | OPERATING MODE INFORMATION | | | | | |
|---|---|---|---|---|---|---|
| | OPERATION A | OPERATION B | OPERATION C | OPERATION D | OPERATION E | ... |
| BLACK AND WHITE COPY | 1 | 0 | 1 | 0 | 1 | ... |
| COLOR COPY | 0 | 1 | 0 | 1 | 0 | ... |
| ONE-SIDE COPY | 1 | 1 | 0 | 0 | 1 | ... |
| DUPLEX COPY | 0 | 0 | 1 | 1 | 0 | ... |
| ORDINARY PAPER COPY | 1 | 1 | 1 | 1 | 0 | ... |
| OHP PAPER COPY | 0 | 0 | 0 | 0 | 1 | ... |
| ... | ... | ... | ... | ... | ... | ... |

FIG. 5

61 62 60

| HEADER INFORMATION | INVERTED WAVEFORM INFORMATION |
|---|---|
| 101010 | INVERTED WAVEFORM INFORMATION A |
| 011010 | INVERTED WAVEFORM INFORMATION B |
| 100110 | INVERTED WAVEFORM INFORMATION C |
| 010110 | INVERTED WAVEFORM INFORMATION D |
| ... | ... |

FIG. 6

NOISE SUPPRESSOR IN IMAGE FORMING APPARATUS AND NOISE SUPPRESSING METHOD

BACKGROUND OF THE INVENTION

1. Field of the Invention

The present invention relates to a noise suppressor in an image forming apparatus and a noise suppressing method making use of a noise suppressing technique, in which in an image forming apparatus such as a laser beam printer, an electronic photographic copying machine and the like, sounds of a waveform reversed to a waveform of noises generated from a noise source are generated and interfered with each other to offset the noises.

2. Description of Related Art

In the past, the noise suppressing technique, in which sounds of a waveform reversed to a waveform of noises generated from a noise source are generated and interfered with each other to offset the noises, has been developed as the technique for suppressing noises, which technique has been applied to a part of products. For example, Japanese Published Unexamined Patent Application No. Hei 2-97877 proposes an example applied to the noise suppressing of noises in a compressor of a domestic refrigerator, and Japanese Published Unexamined Patent Application No. Hei 5-142887 and 6-8581 propose an example applied to a copying machine.

FIG. 14 is a view of assistance in explaining the construction of a noise suppressing system in prior art. In FIG. 14, reference numeral 141 designates a noise source; 142, a duct; 143, a first analog/digital converter (A/D converter); 144, a digital filter; 145, a secondary sound source speaker; 146, an opening of the duct; 147, an error mike; 148, a second analog/digital converter (A/D converter); and 149, a control section.

The noise suppressing operation by the construction of the conventional noise suppressing system will be described with reference to FIG. 14. For the noise source 141 which generates a noise to be suppressed, a space surrounding the circumference of he noise source 141 is formed by the duct 142, and an orientation in a longitudinal direction of the duct 142 is imparted to the noise generated from the noise source 141. A signal correlated to a sound radiated from the noise source 141 such as vibrations of the noise of the noise source 141 is measured, which is formed into a digital signal through the first analog/digital converter 143 and input into the digital filter 144. The digital filter 144 performs the signal processing as described later to output a control output which generates a secondary sound for suppressing noise from the secondary sound source speaker 145. The secondary sound source speaker 145 is driven by the control output, and the secondary sound generated from the secondary sound source speaker 145 interferes with the waveform of the noise generated from the noise source 141 and offsets with each other and is controlled so that sound pressure is "0" at a position (noise suppressing position) leading to outside from the surrounding space of the duct 142, for example, at the opening 146 of the duct. Thereby, the noise radiated from the noise source 141 is suppressed at the noise suppressing position.

Next, the signal processing in the digital filter 144 will be described. The opening 146 leading to outside from the surrounding space of the duct 142 is provided with the error mike 147 for measured a combined sound pressure of a radiated sound from the noise source 141 and a sound to be controlled of the secondary sound from the secondary sound source speaker 145. Let G be the transmission characteristics from the noise source 141 to the error mike 147, C be the transmission characteristics from the secondary sound source speaker 145 to the error mike 147 and F be the transmission characteristics of the first analog/digital converter 143, then the flow of the signal according to the construction of the noise suppressing system shown in FIG. 14 is as shown in FIG. 15.

In the signal channel of the sound from the noise source 141 to the error mike 147, the transmission characteristics including the digital filter 144 of the secondary sound source is represented by $G+C\times W\times F$ as shown in FIG. 15. The values of the transmission characteristics G, C and F are used to constitute the digital filter 144 so that $G+C\times W\times F=0$ is given, that is, the transmission characteristics W is given by $W=-G/(C\times F)$ for suppressing the noise of the noise source 141 at the position of the error mark 147 (noise suppressing position). Since the transmission characteristics F is fixed, the values of the transmission characteristics G and C are presumed by the control section 149 so that the output of the error mark 147 is minimum, and the value of the filter coefficient (transmission characteristics W) in the digital filter 144 is updated.

According to the noise suppressing system making use of the conventional noise suppressing technique as described above, it is necessary for suppressing the noise to perform the detection of noise, presumptive arithmetic operation for the control in the digital filter 144, arithmetic operation of noise and sound of reversed waveform, and production of reversed waveform sound within the time the sound generated from the noise source 141 arrives at the secondary sound source for generating the sound of reversed waveform (secondary sound source speaker 145). Therefore, it is necessary for assuring the time for carrying out these signal processes to provide a fixed distance between the noise source 141 and the secondary sound source speaker 145, and in addition, a high speed signal processing apparatus for signal processing is also necessary.

Accordingly, for applying the construction of the noise suppressing system as described above, it is necessary to provide a large duct for a passage of sound, which unavoidably makes the apparatus larger. Alternatively, it is assumed that a noise is a standing sound such as a sine wave to calculate and produce a reversed waveform. The secondary sound source of the reversed waveform is delayed several periods with respect to the noise waveform to interfere with the noise from the noise source. Thereby, it is possible to shorten the distance between the noise source and the secondary sound source to correspond with the miniaturization of apparatus. However, this is applied to the case where the noise can be presumed as a standing sound but cannot be applied to the noise of transient sound such as a shock sound particularly involved in a copying machine.

Further, in the control used in the aforementioned conventional technique, statistical standing properties of signal used for the control for assuring the stability of applied rule and convergence are demanded. Therefore, in the case where unexpected disturbance involves in the mike or error mike for measuring the noise, there sometimes possibly falls in the unstable state of the entire system and radiates a sound larger than the noise from the noise source. Particularly, in the environment of an office in which a copying machine is installed, much unexpected disturbing sounds such as telephone sounds in the periphery, sounds of a separate noise source within the apparatus and the like are present, thus making impossible to expect the stable noise suppressing effect.

On the other hand, in the case where a parameter of a control system is fixed, there is a problem to correspond with the unevenness of products, change after passage and change in environment. In the operation of the copying machine, its copying modes include operating modes in various recording modes such as an OHP copying mode, a color/black-white copying mode, a duplex copying mode and the like, which often involves the change in properties of noises generated in the operating mode in various recording modes. Therefore, it is difficult to carry out operation corresponding to a fixed parameter.

In addition, it is necessary for securing the on-line property of arithmetic operation of waveforms of a control sound for generating a reversed waveform for suppressing noise to use an expensive digital signal processing (DSP) for performing a high speed signal processing, which is the cause of impairing the lower cost of apparatus.

The present invention has been achieved in order to solve these problems noted above. An object of the present invention is to provide a noise suppressor in an image forming apparatus and a noise suppressing method capable of, in an image forming apparatus such as an electronic photographic copying machine, generating and interfering each other sounds of waveform and reversed waveform of noises generated from drive mechanisms as noise sources and offsetting noises by the technique at less cost and capable of suppressing noises positively and effectively.

SUMMARY OF THE INVENTION

For achieving the aforementioned object, according to the present invention, as a first feature, there is provided a noise suppressor in an image forming apparatus having a drive mechanism as a generating source for noises during operation, comprising: signal detection means for detecting an operation start signal of said drive mechanism, a sound generator for generating a secondary sound of waveform reversed to a waveform of said noise, sound generator control means for generating said secondary sound from said sound generator at a position for suppressing the noise, and timing control means for controlling said sound generator control means at a fixed timing by the detected signal from said signal detection means.

According to the present invention, as a second feature, there is provided a noise suppressor in an image forming apparatus having a drive mechanism as a generating source for noises during operation, comprising: operating timing memory means for recording operating timing information of the drive mechanisms in various operating modes of the image forming apparatus, discrimination means for discriminating the operating modes of the image forming apparatus, timing reading means for reading the operating timing information of said drive mechanisms corresponding to the operating modes discriminated by said discrimination means, a sound generator for generating a secondary sound of a waveform reversed to a waveform of said noise, sound generator control means for performing the control for generating said secondary sound from said sound generator at a position for suppressing the noise, and timing control means for controlling said sound generator control means on the basis of the operating timing information read by said timing reading means.

According to the present invention, as a third feature, there is provided a noise suppressor in an image forming apparatus, wherein said sound generator control means having waveform memory means for storing at least waveform information of a waveform reversed to a waveform of a noise generated from said drive mechanism, and reading means for reading waveform information stored in said waveform memory means.

According to the present invention, as a fourth feature, there is provided a noise suppressor in an image forming apparatus, further comprising: transmission characteristics measurement means for measuring transmission characteristics of the secondary sound transmitted to a position where the secondary sound generated from said sound generator suppresses the noise, said sound generator control means changing a phase or an amplitude of said secondary sound on the basis of the transmission characteristics of the measured result of said transmission characteristics measuring means. According to a fifth feature, there is provided initial state setting means for setting an operation start position of said drive mechanism to an initial state.

According to the present invention, as a sixth feature, there is provided a noise suppressing method in an image forming apparatus, comprising: in a noise suppressor in an image forming apparatus having a drive mechanism as a generating source for noises during operation, detecting an operation start signal of said drive mechanism, generating a secondary sound of a waveform reversed to a waveform of a noise generated from said drive mechanism on the basis of said operation start signal, and interfering the noise generated from said drive mechanism with said secondary sound at the noise suppressing position to suppress the noise.

According to the present invention, as a seventh feature, there is provided a noise suppressing method in an image forming apparatus, comprising: in a noise suppressor in an image forming apparatus having a drive mechanism as a generating source for noises during operation, storing operating timing information of said drive mechanisms in various operating modes for forming an image, discriminating an operating mode for forming an image by the start of forming an image, reading the operating timing information of said drive mechanism corresponding to said discriminated operating mode, generating a secondary sound of a waveform reversed to a waveform of a noise generated from said drive mechanism from a sound generator on the basis of the read operating timing information, and interfering the noise generated from said drive mechanism with said secondary sound to suppress the noise.

According to the present invention, as an eighth feature, there is provided a noise suppressing method in an image forming apparatus, further comprising: setting the operation start position of said drive mechanism to an initial state prior to the start of operation. According to a ninth feature, the method comprises measuring the transmission characteristics of the secondary sound from the installed position of said sound generator to the noise suppressing position, and changing a phase or an amplitude of said secondary sound on the basis of the transmission characteristics of the measured result.

The present invention has various features as noted above. In the noise suppressor in an image forming apparatus according to the first feature, the image forming apparatus has the drive mechanism for performing the essential recording operation but each drive mechanism is a generating source of noise during operation, and the noise suppressor performs the noise suppressing operation for suppressing the noise from the drive mechanism. Here, there is provided a sound generator for generating a secondary sound of a waveform reversed to a waveform of noise, and the sound generator control means controls the sound generator and performs the control for generating the secondary sound from the sound generator at the position where the noise is suppressed. In this control, the signal detection means detects the operation start signal of the drive mechanism and the timing control means controls the sound generator control means at a fixed timing by the detected signal from the signal detection means.

Thereby, the noises generated from the drive mechanisms for performing the recording operation are interfered and offset each other by the secondary sound of a waveform reversed to a waveform of the noise generated from the sound generator to suppress the noise. That is, with respect to the noises from the drive mechanisms caused by the operation of the copying machine, similar noises are generated corresponding to the recording operation. Thus, attention has been paid to the repeatability of such generation of noises and the standing property in a sense of statistic of the noise waveform. For obtaining the reversed waveform with respect to the noise waveform, the DSP circuit for the calculation on the on-line is not used for calculation but the noises generated in the respective operating timings are measured in advance on the on-line to obtain the secondary sound reversed in waveform to the noise, which is stored in the memory. Then, the secondary sound is read matching to the operating timing of the drive mechanism and interfered with the noise to suppress the noise.

For positively and efficiently reducing the noises of this kind generated from the drive mechanisms of the copying machine, data of reversed waveform of the operating sound of the drive mechanism is read from the memory corresponding to the operation of the drive mechanism, and the noises are radiated from the secondary sound source speaker at the respective operating timings and interfered with the waveform of the noise to reduce the noise.

In the noise suppressor in an image forming apparatus according to the second feature of the present invention, the operating timing information of the drive mechanisms in the respective operating modes of the image forming apparatus is stored by the operating timing memory means, the operating modes of the image forming apparatus are discriminated by the discrimination means, and the operating timing information of the drive mechanism corresponding to the operating mode discriminated by the discrimination means is read by the timing reading means. The sound generator control means controls the sound generator for generating the second sound of the waveform reversed to the waveform of the noise to perform the control for generating the secondary sound from the sound generator at the position where the noise is suppressed. This control is effected by the timing control means. That is, the timing control means controls the sound generator control means on the basis of the operating timing information read by the timing reading means to suppress the noises generated by the respective drive mechanisms.

In this way, the operating modes of the copying machine input by an operator are discriminated, and a timing chart of operating modes discriminated from a time table in which operating timings of the drive mechanisms of the operating modes are stored in advance are selected. In reducing the noises, data of a waveform reversed to the noise is read from the memory linking with the selected timing chart, and in the operating timing of the drive mechanism, the sound is radiated from the secondary sound source speaker to interfere with the noise waveform to offset each other to reduced the noises.

According to the third feature of the present invention, for reducing further positively and efficiently the noise generated by the drive mechanism of the copying machine, the sound generator control means comprises the waveform memory means and the reading means. The waveform memory means stores therein the reversed waveform information of a waveform reversed to a waveform of the noise generated at least from the drive mechanism, and the reading means reads the waveform information stored in the waveform memory means.

According to the fourth feature, likewise, for reducing further positively and efficiently the noise, transmission characteristics measuring means is provided. The noise at the noise suppressing point and the transmission characteristics from the secondary sound source to the noise suppressing point are measured every fixed period, and the sound generator control means changes the phase or amplitude of the secondary sound on the basis of the transmission characteristics of the transmission characteristics measuring means on the basis of the measured result of the transmission characteristics measuring means. The waveform information for suppressing or reducing the noise making use of the interference of the sound is arithmetically operated from the measured result by the transmission characteristics measuring means, and the result of operation is compared with the content stored in the waveform information memory means. If determination is made by a fixed determination reference such that both are different from each other, the wave information stored in the waveform information memory means is updated. Thereby, the effect for further reducing the noise is obtained.

According to the fifth feature of the present invention, there is provided the initial state setting means for setting the operation start position of the drive mechanism as the noise source for generating the noise to the initial state. The initial state setting means maintains the initial state in the case where the drive mechanism of the noise source is operated, for example, maintains, in the case where the drive mechanism of the noise source is a rotary body, a rotation start angle to a fixed positional state. The noise generated from the drive mechanism is always generated as a waveform of the same phase from the start of operation.

To this end, the noise generated by the drive mechanism of the noise source is measured in advance according to the initial state of the respective drive mechanism and the drive timing of the drive mechanism, and the secondary sound of a waveform reversed to the noise is obtained and stored in the waveform information memory means. The waveform information can be used to further enhance the noise reducing effect. When the noise from the noise source is reduced, the data of the reversed waveform information is read linking with the progress of the operating time of the copying machine, and the sound is radiated from the secondary sound source speaker at the respective operating timing to interfere with the noise waveform and offset each other to reduce the noise.

According to the noise suppressor in the image forming apparatus of the present invention, the on-line property is not necessary for calculating the secondary sound waveform, so-called control waveform for offsetting the noise by the interference. Therefore, the time required to produce a waveform of a control sound is only the time read from the memory means. It is thus not necessary to gain the distance between the noise source and the secondary sound source, and accordingly, the high speed arithmetic operating apparatus such as a DSP circuit is not necessary. Therefore, it is possible to realize an image forming apparatus provided with a noise suppressor at less cost.

Also, with respect to the transient noise such as a shock sound that could not be processed in the on-line in terms of the calculation time even by the high speed arithmetic processing apparatus such as a DSP circuit, it is possible to easily cope therewith merely by reading information of the noise waveform stored in advance at a timing matched to the generation of the noise. Further, since adaptable calculation is not made, the instability of the control system caused by the disturbance can be avoided.

With respect to the noise waveform caused by the difference in the operating mode of the copying machine that cannot be handled by the fixed parameter with respect to various noises caused by the noise source of the drive mechanisms of the image forming apparatus, it can be treated by selecting the data of the reversed waveform information corresponding to the drive timing chart of the drive mechanism of the noise source prepared every operating mode of the copying machine and the noises of the drive mechanisms. Further, since the selection of the operating mode can be decided by the operation of designating the copying mode by the operator, it is not necessary to provide a mike for recognizing a change in each noise source.

Further, a variation which is gentle in time such as a change after passage, a change in environment or the like can be treated by updating the variation every fixed period by measuring the space transmission characteristics from the sound source of the noise of the drive mechanism to the noise suppressing point. This updating processing may be carried out when the machine is under maintenance operation or may be automatically carried out.

BRIEF DESCRIPTION OF THE DRAWINGS

FIG. 5 is a view showing one example of the data construction of an operating mode data base;

FIG. 6 is a view of assistance in explaining the data construction of a memory for storing reversed waveform information of a plurality of noises;

DESCRIPTION OF THE PREFERRED EMBODIMENTS

Figure 1:
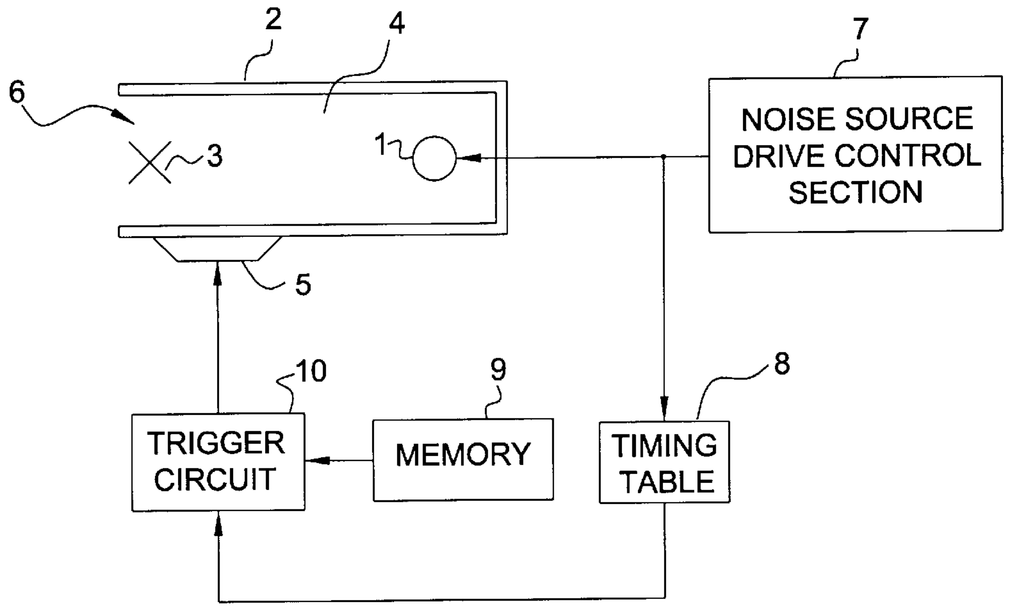
FIG. 1 is a block diagram of assistance in explaining the construction of a noise suppressor in an image forming apparatus according to a first embodiment of the present invention.
Figure 2:
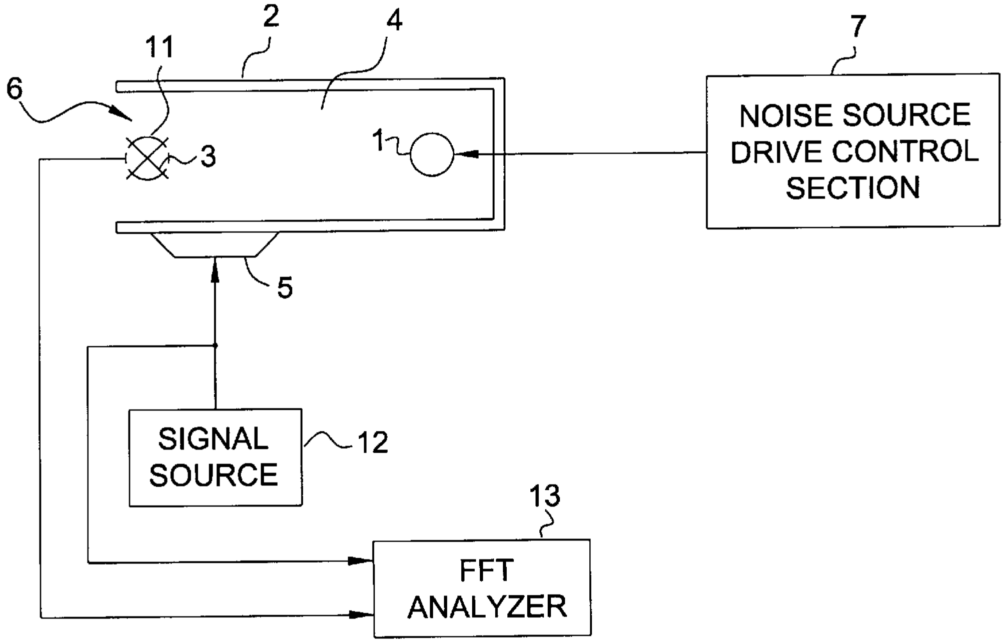
FIG. 2 is a view of assistance in explaining the system construction for measuring the transmission characteristics of noises.

The preferred embodiments of the present invention will be described in detail hereinafter with reference to the accompanying drawings. FIG. 1 is a block diagram of assistance in explaining the construction of a noise suppressor in an image forming apparatus according to a first embodiment of the present invention. FIG. 2 is a view of assistance in explaining the system construction for measuring the transmission characteristics of noises. In FIGS. 1 and 2, reference numeral 1 designates a noise source of a drive mechanism in an image forming apparatus; 2, a duct constituting a passage of noise; 3, a noise suppressing point; 4, a space of the duct; 5, a secondary sound source speaker for generating a control noise (a secondary noise) for noise suppression; 6, a duct opening; 7, a noise source drive control section; 8, a timing table; 9, a memory for storing reversed waveform information for suppression of noise corresponding to each noise source; 10, a trigger circuit for reading out reversed waveform at a designated timing from the memory; 11, a sensor mike; 12, a signal source for generating white noise; and 13, an FFT analyzer for frequency response analysis.

In the case where the noise suppressor of the present invention is applied to a copying machine of the image forming apparatus, the noise source 1 is a drive mechanism for carrying out the copying operation (such as a feed roller, an original read and scanning mechanism, a drive motor, a photosensitive drum, a charge roller, a cooling fan, etc.), and the noise source drive control section 7 is a control section for controlling the drive mechanism.

The duct 2 for surrounding the periphery of the noise source 1 may be of a suitable length in a longitudinal direction of the duct 2 because there is no restriction in time of on-line computation for computation of reversed waveform and computation of transmission characteristics. However, there is restriction that since the length in a longitudinal direction of the duct 2 leads the noise to be suppressed to the noise suppressing point for orientation in a direction of propagation of soundwave, the sectional shape thereof should be in the range in which the soundwave radiated from the noise source 1 is regarded as a plane wave.

In order to store the noise suppressing reversed shape corresponding to the noise source in the memory 9, the transmission characteristics of the noise is first measured. The system construction for measuring the transmission characteristics of the noise will be explained with reference to FIG. 2. In the case where the transmission characteristics of sound from the secondary sound source speaker 5 to the preset noise suppressing point 3 are measured, the white noise output from the signal source 12 is reproduced by the secondary sound source speaker 5, as shown in FIG. 2, the sound at the position to which the white noise is transmitted, that is, the sound in which the white noise is reflected by the transmission characteristics of the space 4 of the duct 2 is detected by the sensor mike 11, and the frequency response analysis is effected by the FFT analyzer 13.

Next, at the same time, the noise from the noise source 1 at the noise depressing point 3 is measured. In the measurement in this case, preferably, the point for measuring the transmission characteristics of the secondary sound source and the point for measuring the noise of the noise source is the geometrically same point, but it may be substantially within the range represented by the following expression:

$$-0.085\ \lambda < \text{error in position therebetween} < 0.075\ \lambda$$

wherein λ is the wavelength of the noise source.

A waveform (reversed waveform) offsetting the noise is obtained so as to have a waveform reversed to the noise of the noise source 1 at the noise suppressing point 3 is obtained from the noise of the noise source 1 at the noise suppressing point 3 and the transmission characteristics from the secondary sound source speaker 5 to the noise suppressing point 3, and information of the obtained waveform is stored in the memory 9.

The reversed waveform of the noise is obtained in a manner as described above. The processing of the step for obtaining the reversed waveform of the noise is carried out by one of the steps for manufacturing a copying machine of the image forming apparatus provided with the aforementioned noise suppressing apparatus or carried out at the time of maintenance at a location where a copying machine of the image forming apparatus provided with the aforementioned noise suppressing apparatus is installed. Accordingly, in the noise suppressor according to the present invention, it is not necessary to perform the arithmetic operation for obtaining the reversed waveform of the noise in the processing on the on-line. Further, a parameter of the waveform information of the reversed waveform obtained is not updated but fixed except at the time of maintenance. According to the experiments made by the inventors, even if the parameter is fixed, if the characteristics of the secondary sound is in the range represented by the following expression at the noise suppressing point, the noise suppressing effect is not materially deteriorated.

$$0.5 < \text{amplitude of secondary sound/amplitude of noise} < 1.5$$

Further, it has been confirmed from the experimental results that with respect to a change in temperature, at a room temperature of 25° C., the effect of noise suppressing performance is assured in a wide range of about ±10° C.

Figure 3:
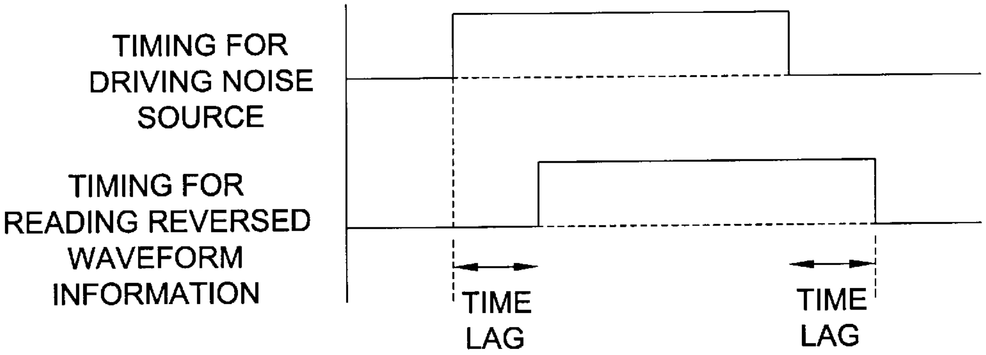
FIG. 3 is a view of assistance in explaining the timing for driving a noise source and the read-out timing of reversed waveform information.

The relation between the drive timing of the noise source 1 and the read timing from the memory 9 is held by the timing table 8. A fixed time lag (the time in which the noise is propagated within the duct) is provided between the noise source drive timing and the read timing of the reversed waveform information, in accordance with the content of the timing table 8, as shown in FIG. 3, corresponding to a drive order signal output from the noise source drive control section 7 for controlling the drive mechanism to be the noise source 1 during operation to actuate the trigger circuit 10 for reading information from the memory 9. The trigger circuit 10 accesses to the memory 9 to read the information of reversed waveform corresponding to the noise of the noise source 1 at present and drive the second sound source speaker 5, in accordance with the content of the timing table 8 (timing chart).

Between the drive timing of the drive mechanism of the noise source 1 and the read timing, there is a time difference according to a phase determined by the acoustic transmission characteristics from the noise source to the noise suppressing point and the acoustic transmission characteristics from the secondary sound source speaker to the noise suppressing point, and information relating thereto is also stored in advance in the timing table 8.

When the trigger circuit 10 is actuated, a signal caused by the information of reversed waveform read from the memory 9 is fed to the secondary sound source speaker 5, and a sound of reversed waveform (control sound: secondary sound) is reproduced from the secondary sound source speaker 5 so as to offset with the noise from the noise source 1 at the noise suppressing point 3. As a result, two soundwaves are propagated through the space 4 in the duct 2, transmitted while interfering, offset each other and suppressed at the noise suppressing point 3. Even in the case where amplitudes and phases of two soundwaves of polarities reversed to each other are not coincided, the magnitude of the noise is considerably reduced.

Figure 4:
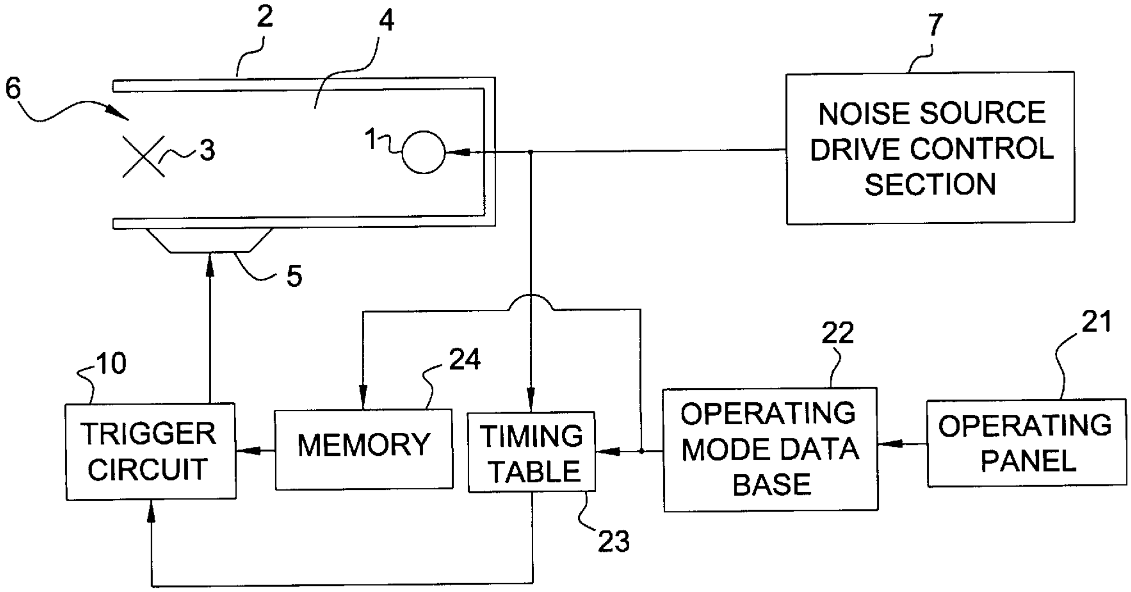
FIG. 4 is a block diagram showing the construction of a noise suppressor in an image forming apparatus according to a second embodiment of the present invention.

The second embodiment will be described hereinafter. FIG. 4 is a block diagram showing the construction of a noise suppressor in an image forming apparatus according to a second embodiment of the present invention. In FIG. 4, reference numeral 1 designates a noise source of a drive mechanism of the image forming apparatus; 2, a duct which is a passage of sound; 3, a noise suppressing point; 4, a space of the duct; 5, a secondary sound source speaker for generating a control sound (a secondary sound) for suppression of noise; 6, a duct opening; 7 a noise drive control section; and 10, a trigger circuit for reading a reversed waveform from a memory at a designated timing. These parts are the same as those in the first embodiment. Further, reference numeral 21 designates an operating panel; 22, an operating mode data base; 23, a timing table for storing operating timing information in the respective operating modes; and 24, a memory for storing reversed waveform information for suppressing noise corresponding to the operation (noise source) of the drive mechanism in the respective operating modes.

The noise depressor according to the second embodiment is provided with the operating panel 21 and the operating mode data base 22 in addition to those provided in the first embodiment (FIG. 1). The timing table 23 and the memory 24 store operating timing information in the respective operating modes corresponding to operating modes of a copying machine and reversed waveform information for suppressing noise. The operating panel 21 is an interface apparatus for designating an operator copying modes, for example, such as black and white copies, color copies, duplex copies, etc. The operating mode data base 22 is a data base for reading operating mode information which specifies a timing of control by which drive mechanisms are operated in the case where copying operations are carried out which correspond to copying modes of the copying machine designated by an operator through the operating panel 21.

Information of the copying mode selected by the operator through the operating panel 21 is fed to the operating mode data base 22. In the operating mode data base 22, information of the operating mode at the operating timing at which the drive mechanisms within the copying machine are operated corresponding to the copying modes of the copying machine designated by the operator. FIG. 5 is a view showing one example of the data construction of the operating mode data base. In FIG. 5, reference numeral designates the content of the operating mode data base; 51, operating mode information; 52, the designated function.

As shown in FIG. 5, the content 50 of the operating mode data base 22 is that with respect to the operating mode information 51, the flag “1” is erected for the designated copying function indicative of the kind of the designated functions 52 of the designated copying functions according to the designated copying operation, which is discriminated by the concrete content of the respective operating modes. That is, this will be explained in detail by way of an example shown in FIG. 5, in the operation A, the flag “1” is erected on columns of black and white copy, one-side copy and ordinary paper copy representative of the kind of the designated functions 52, which is the normal copying operating mode. In the operation B, the flag “1” is erected on columns of color copy, one-side copy and ordinary paper copy representative of the kind of the designated functions 52, which is the color copying operating mode. Similarly, in the operation C, the duplex copying operating mode of normal copying (black and white copying) is shown, and in the operation D, the duplex copying operating mode of the color copying is shown.

The content of the copying operation in the corresponding operating mode is specified, and the content of the operating timing of the drive mechanism relating to the specified operation is recognized by the content of the operating mode information 51. The operating mode information 51 obtained from the operating mode data base 22 in accordance with the designation of the operating panel 21 is fed to the timing table 23 and the memory 24. The timing table 23 and the memory 24 selects and specifies the kinds of operating timing information of the drive mechanisms and information for reading reversed waveform information in accordance with the contents of operating mode information (copying modes) obtained from the operating data base 22.

That is, in the copying machine, the respective drive mechanisms for performing its copying operation are actuated in accordance with the copying mode designated by the operator on the operating panel 21 to effect the operation in the designated copying operating mode. In this case, the kind of the noise waveform caused by the operation of the respective drive mechanisms can be specified corresponding to the copying modes designated by the operating panel 21. Therefore, in the second embodiment, the kinds of the operating timing information of the drive mechanisms to be a noise source for suppressing the noise of the copying operation and the information for reading the reversed waveform information for suppressing the noise are selected and specified in accordance with the copying modes designated by the operating panel 22 prior to the operation of the copying machine. The noise generated when the copying machine is actuated in the specific copying mode designated by the operator is suppressed by the operation of the function of the timing table 23 caused by the operating timing information selected and read and the function of the memory 24 for reading the selected reversed waveform information.

Next, the operation for suppressing the noise according to the designated copying operating mode will be described in detail. FIG. 6 is a view of assistance in explaining the data construction of a memory for storing reversed waveform information of a plurality of noises. In the noise suppressor in the image forming apparatus according to the second embodiment, since the noise generated according to the respective copying operation according to the designated copying modes is suppressed, the reversed waveform information of a plurality of noises are stored. Because of this, as shown in FIG. 6, by the data construction 60 of the memory for storing reversed waveform information of noises, inverted waveform information 62 of the reversed waveform information of noises are stored with operating mode information (51; FIG. 5) corresponding to the designated copying operating mode being header information 61. That is, this data construction is that the operating mode information 51 from the operating mode data base 22 is used as the header information 61, and the header information 61 is addressed to read the inverted waveform information 62. In the case where the inverted waveform information 62 is accessed by the operating mode information (header information) from the memory 24 constructed by the data construction as described, the header information 61 of the data construction 60 is compared with an operating mode signal fed along with the header information 61 of the data construction 60 to determine the operating timing information read from the timing table 23 and the inverted waveform information 62 read from the memory 24.

When the copying operation is started according to the designated copying mode, the respective drive mechanisms (noise source) are actuated to generate the noise. In this case, the trigger circuit 10 for reading the reversed waveform information of noise from the memory 24 is actuated corresponding to the drive order signal output from the noise source drive control section 7. By the operation of the trigger circuit 10, the signal of the reversed waveform information read from the memory 9 is fed to the secondary sound source speaker 5, and sound of the reversed waveform information is reproduced so that the noise from the noise source 1 is suppressed at the noise suppressing point 3. Two sounds are propagated while interfering with each other and offset each other to suppress the noise at the noise suppressing point 3.

Figure 7:
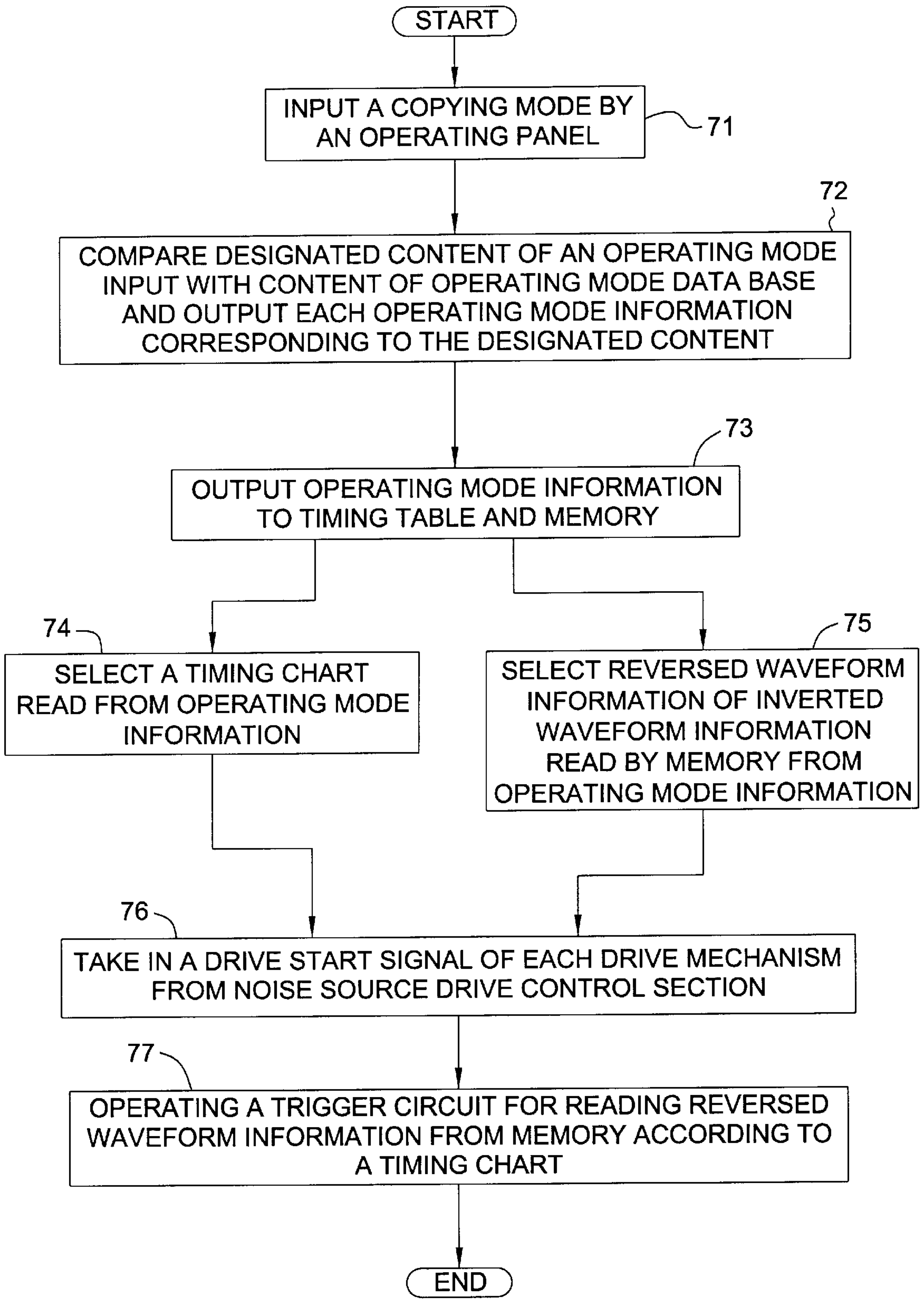
FIG. 7 is a flow chart showing the processing flow of noise suppressing operation in the noise suppressor according to the second embodiment.

FIG. 7 is a flow chart showing a processing flow of noise suppressing operation in the noise suppressor according to the second embodiment. The operation of the noise suppressor according to the second embodiment will be described with reference to the flow chart of FIG. 7. In the noise suppressing operation, first, in Step 71, a copying mode is input by the operating panel. Next, in Step 72, the designated content of the copying mode input is compared with the content of the operating mode data base to output the operating mode information corresponding to the designated content. Then, in Step 73, the operating mode information are output to the timing table and the memory.

With this, in Step 74, in the timing table, a timing chart to be read is selected according to the operating mode information. At this time, in Step 75, the memory selects the reversed waveform information of the inverted waveform information read by the memory according to the operating mode information. Then, in Step 76, drive start signals of the respective drive mechanisms from the noise source drive control section are taken in. Then, in Step 77, the trigger circuit for reading the reversed waveform information from the memory is actuated in accordance with the timing chart. Thereby, the sound caused by the signal of the reversed waveform information from the secondary sound source speaker is reproduced, and two sounds, i.e., the noise from the noise source 1 and the reproduced sound, are propagated while interfering each other, and offset each other to suppress the noise at the noise suppressing point.

The reversed waveform information of the noise waveform read from the memory correspond to the noises generated from the respective drive mechanisms of the copying machine. However, since the change in noise caused by the change after passage of the copying machine reflects on the reversed waveform information of the noise waveform, and since the change in noise caused by environment according to the installation place of an office provided with the noise suppressor reflects on the reversed waveform information of the noise waveform, it is desirable to update the reversed waveform information stored in the memory. Next, the embodiment of the present invention constructed such that the reversed waveform information stored in the memory can be updated will be described as the third embodiment.

Figure 8:
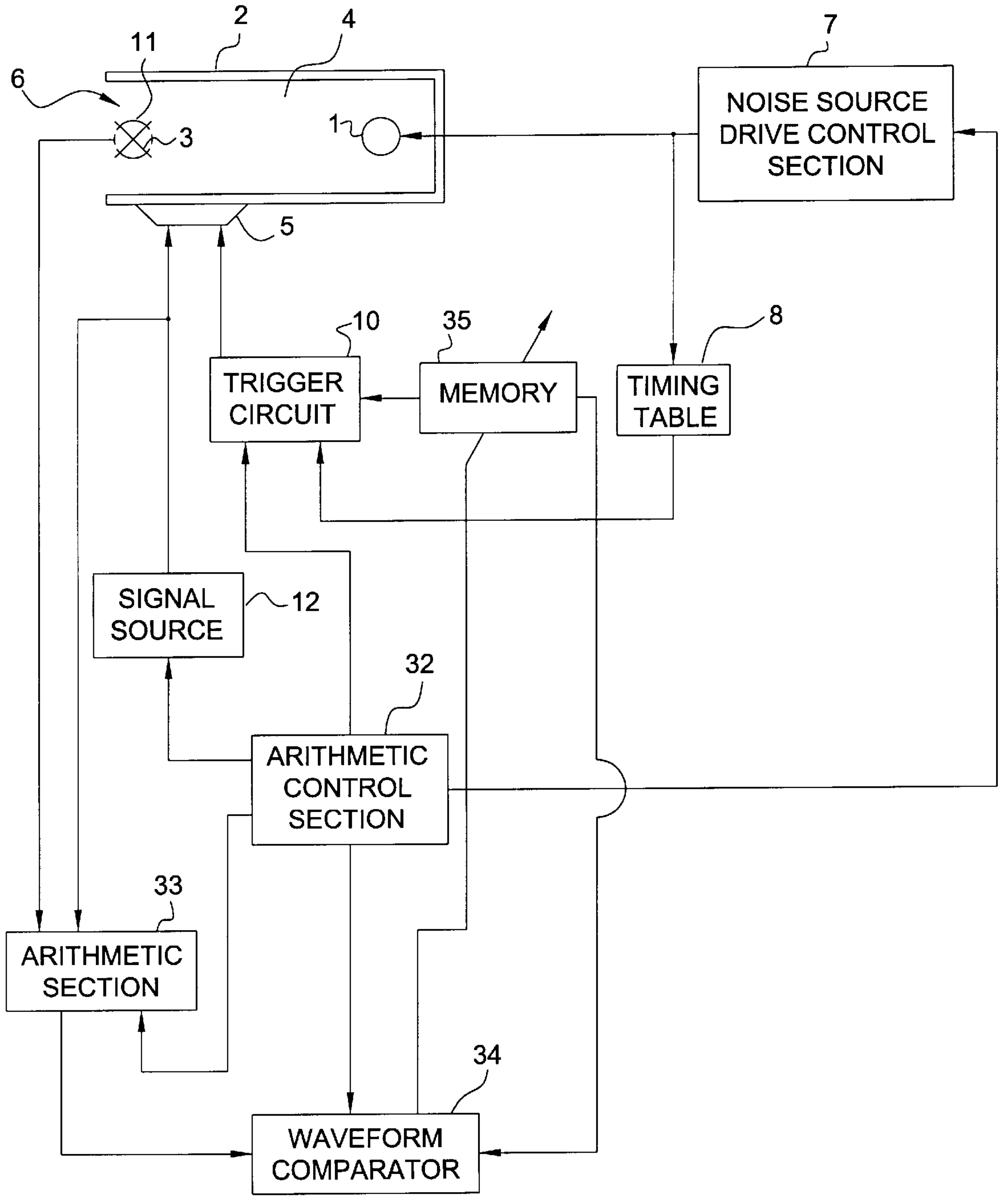
FIG. 8 is a block diagram of assistance in explaining the construction of a noise suppressor in an image forming apparatus according to a third embodiment of the present invention.

FIG. 8 is a block diagram of assistance in explaining the construction of a noise suppressor in an image forming apparatus according to a third embodiment of the present invention. In FIG. 8, reference numeral 1 designates a noise source of each drive mechanism in an image forming apparatus; 2, a duct which is a passage of sound; 3, a noise suppressing point; 4, a space of the duct; 5, a secondary sound source speaker for generating a control sound (secondary sound) for suppressing noise; 6, a duct opening; 7, a nose source drive control section; 8, a timing table; 10, a trigger circuit for reading a timing for designating a reversed waveform from a memory; 11, a sensor mike; and 12, a signal source for generating a white noise signal. These are the same as those mentioned in the first embodiment (FIGS. 1 and 2). Reference numeral 32 designates an arithmetic operating control section; 33, an arithmetic operating section; 34, a waveform comparator; and 35, a memory for storing noise suppressing reversed waveform information of noises corresponding to the operation of the drive mechanisms (noise sources).

In the noise suppressor according to the third embodiment, the noise suppressing system further comprises, in addition to the construction of the first embodiment (FIG. 1), a sensor mike 11, a signal source 12 for generating a white noise signal as a reference signal for measuring acoustic characteristics, an arithmetic operating control section 32, an arithmetic operating section 33, a waveform comparator 34, and a memory 35 capable of updating noise suppressing reversed waveform information of noise already stored.

In the noise suppressor according to the third embodiment, the reversed waveform information stored in the memory 35 is updated so that the relation of the reversed waveform is always accurately established with respect to the sound waveform of noise from the noise source 1 at the noise suppressing point 3 in order to correspond to the change in acoustic transmission characteristics caused by the change in characteristics such as installation environment of apparatus and the change after passage of the drive mechanism as a noise source. Because of this, in the noise suppressor according to the third embodiment, the sensor mike 11 is provided at the noise suppressing point 3 so that the reversed waveform information of noise stored in the memory 35 is updated in accordance with the noise waveform detected by the sensor mike 1 and the waveform information of the acoustic transmission characteristics caused by the white noise.

In this case, updating is not accomplished by obtaining an error in the on-line arithmetic operation using a high speed arithmetic operating digital filter such as a DSP circuit as in the conventional noise suppressor but in the noise suppressor according to the third embodiment of the present invention, the arithmetic operating control section 32 controls the noise source drive control section 7, the trigger circuit 10, the signal source 12, the arithmetic operating section 33 and the waveform comparator 34 to update the reversed waveform information stored in the memory 35 so that the noise waveform and the acoustic transmission characteristics at the noise suppressing point 3 are measured by the sensor mike 11 every fixed period to form a waveform reversed to the noise waveform from the noise source 1 by the on-line arithmetic operation.

In updating the noise waveform stored in the memory 35, the arithmetic operation start order is output every fixed period from the arithmetic operating control section 32 to the signal source 12, the arithmetic operating section 33, the noise source drive control section 7 and the trigger circuit 10. In the trigger circuit 10, when the arithmetic operation start order is input from the arithmetic operating control section 32, the signal reading from the memory 35 stops, and in the noise source drive control section 7, the driving of the drive mechanisms as the noise source are stopped.

On the other hand, in the signal source 12, when the arithmetic start order from the arithmetic operating control section 32 is input, the white noise signal is output, it is then reproduced by the secondary sound source speaker 5 and detected by the sensor mike 11 provided at the noise suppressing point of the opening 6. The thus detected acoustic signal (acoustic transmission characteristics) is input in the arithmetic operating section 33. Thereafter, the arithmetic operating control section 32 stops outputting of the white noise signal of the signal source 12, outputs the drive start order signal to the noise source drive control section 7, and restarts the driving of the drive mechanism as the noise source 1. The noise propagated over the space 4 of the duct 2 from the noise source 1 is detected by the sensor mike 11. At this time, the noise waveform detected by the sensor mike 11 is input in the arithmetic operating section 33.

The arithmetic operating section 33 obtains the transmission characteristics from the secondary sound source speaker 5 to the sensor mike 11 and the noise waveform reversed in waveform to the noise of the noise source 1 in the sensor mike 11 in accordance with the arithmetic operation start order, the result of operation of which is stored as the reversed waveform information in the memory 35. In this case, the operation result of the noise waveform reversed in waveform to the noise from the noise source 1 obtained by the arithmetic operating section 33 is compared with the noise waveform of reversed waveform information already stored in the memory 35 by the waveform comparator 34. For example, the waveform comparison is carried out taking a mutual relation between both the waveforms.

Only in the case where as the result of comparison, different waveforms are regarded to be present according to a fixed determination reference, data preservation (updating) of the reversed waveform information to the memory 35 is effected. In the updating in this case, preferably, the arithmetic operation of the noise waveform for obtaining the reversed waveform information by the arithmetic operating section 33 is carried out a few times, and the averaging processing of the results of operation is carried out so that the waveform comparison is not affected by the temporary change in waveform caused by the external noise or the like. When the arithmetic operation of the reverse waveform by the arithmetic operating section 33 and the storing of data in the memory 35 are completed, the signal read restart order of the memory 35 is issued to the trigger circuit 10 from the arithmetic operating control section 32 so that the signal reading from the memory 35 is restarted.

Figure 9:
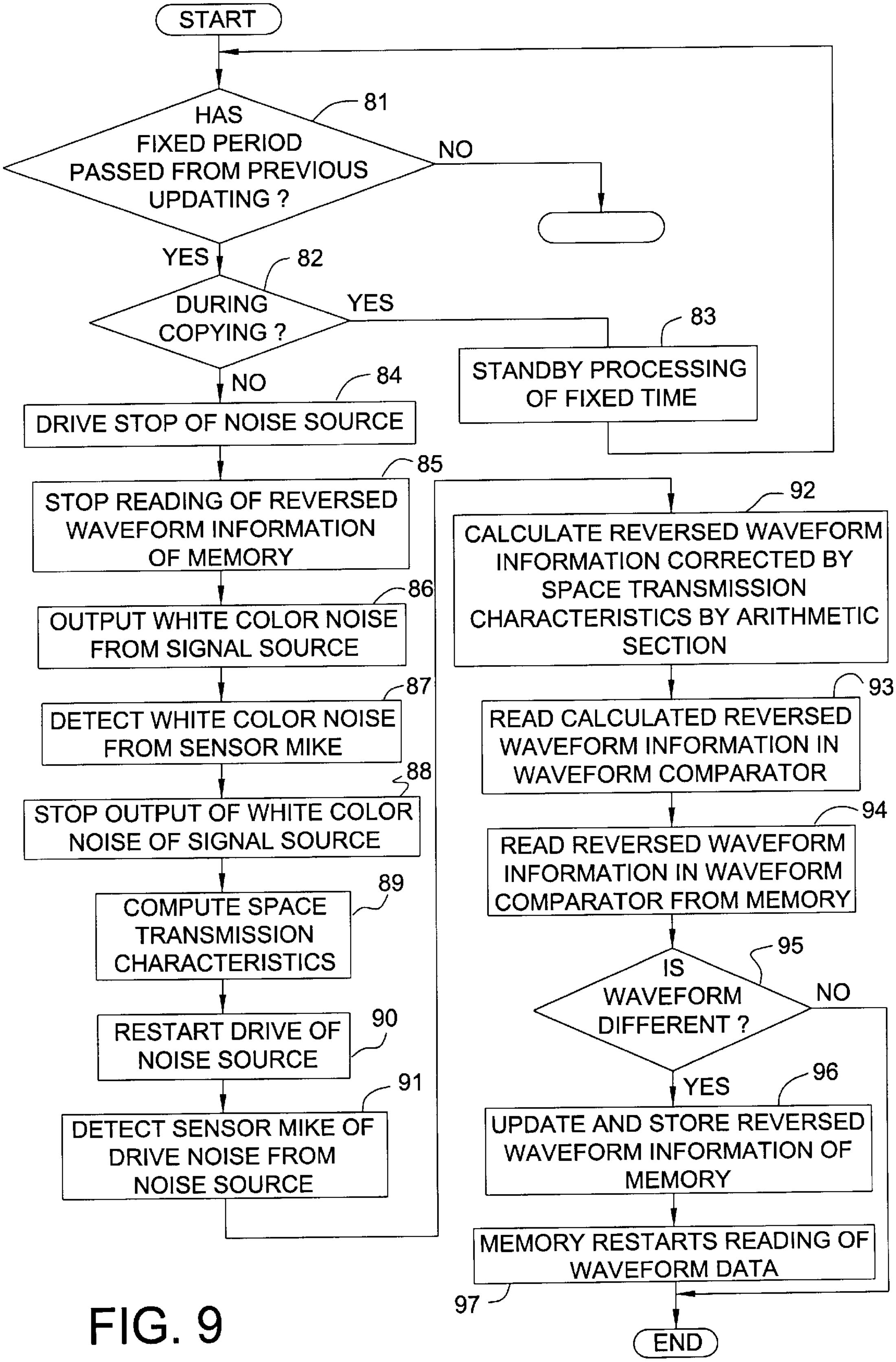
FIG. 9 is a flow chart showing the processing flow for processing of updating reversed waveform information of a memory in the noise suppressor according to the third embodiment.

FIG. 9 is a flow chart showing the processing flow for processing of updating reversed waveform information of a memory in the noise suppressor according to the third embodiment. The operation of the processing flow for processing of updating reversed waveform information of a memory will be described with reference to the flow chart of FIG. 9. In the processing of updating reversed waveform information, when the processing starts, first, in Step 81, whether or not a fixed period has passed since the previous updating is determined. If a fixed period has not passed since the previous updating, the processing is terminated. If a fixed period has passed since the previous updating in the determination in Step 81, the step proceeds to Step 82, where whether or not the present state of the copying machine is during copying is determined. If the state is during copying, the step proceeds to Step 83 where after the standby processing for a fixed time till the copying operation is terminated, the step returns to Step 81 where the processing from Step 81 is repeated.

When the fact that the state is not during copying is determined in Step 82 is determined, the step proceeds to Step 84, and the processing of updating reversed waveform information of the memory is carried out in the processing in Step 84. Therefore, first, in Step 84, the noise source (drive mechanism) is stopped to drive. In Step 85, reading of reversed waveform information of the memory stops. Then, in Step 86, a white noise is output from the signal source. Thereby, a sound of white noise is radiated into the duct 2 from the secondary sound source speaker 5. Therefore, the white noise affected by the acoustic transmission characteristics of the duct is detected by the sensor mike 11 disposed at the noise suppressing point.

In Step 87, the white noise from the duct is detected by the sensor mike. In next Step 88, the output of the white noise of the signal source stops. In next Step 89, the space transmission characteristics of sound which transmits through the duct are calculated. The space transmission characteristics are obtained by arithmetic-operating the reversed waveform of the signal waveform of the white noise obtained by the sensor mike. In Step 90, the drive of the noise source restarts, and in Step 91, the noise transmitted from the noise source is detected by the sensor mike. In Step 92, the reversed waveform corrected by the space transmission characteristics is calculated in the arithmetic operating section.

The reversed waveform information has been obtained the foregoing processing. Next, in Step 93, the reversed waveform information calculated in the waveform comparator is read from the arithmetic operating section. In Step 94, the reversed waveform information prior to updating is read to the waveform comparator from the memory. In Step 95, whether or not the waveform is different is determined from the compared results of the waveform comparator. If the waveform is not different, the reversed waveform information is not necessary for updating. The processing is then terminated.

In the determination in Step 95, if the waveform is different, the reversed waveform stored in the memory is updated to one calculated. Thus, in Step 96, the calculated reversed waveform information is updated and stored in the memory. In Step 97, reading of the reversed waveform information restarts from the memory. With this, the operation for suppressing the noise is carried out making use of the updated reversed waveform information.

The phase of the noise generated by the operation of the drive mechanisms as the noise source depends on the initial position of the operating drive mechanism (the operation start position). Therefore, in the noise suppressing method according to the principle in which the reversed waveform information of the noise from the memory is read and suppressed, if an attempt is made to suppress the noise with more accuracy, preferably, the drive start position of the drive mechanism is always at a fixed position in order to match the phase with the noise. The thus constructed noise suppressor of the image forming apparatus will be described as a fourth embodiment.

Figure 10:
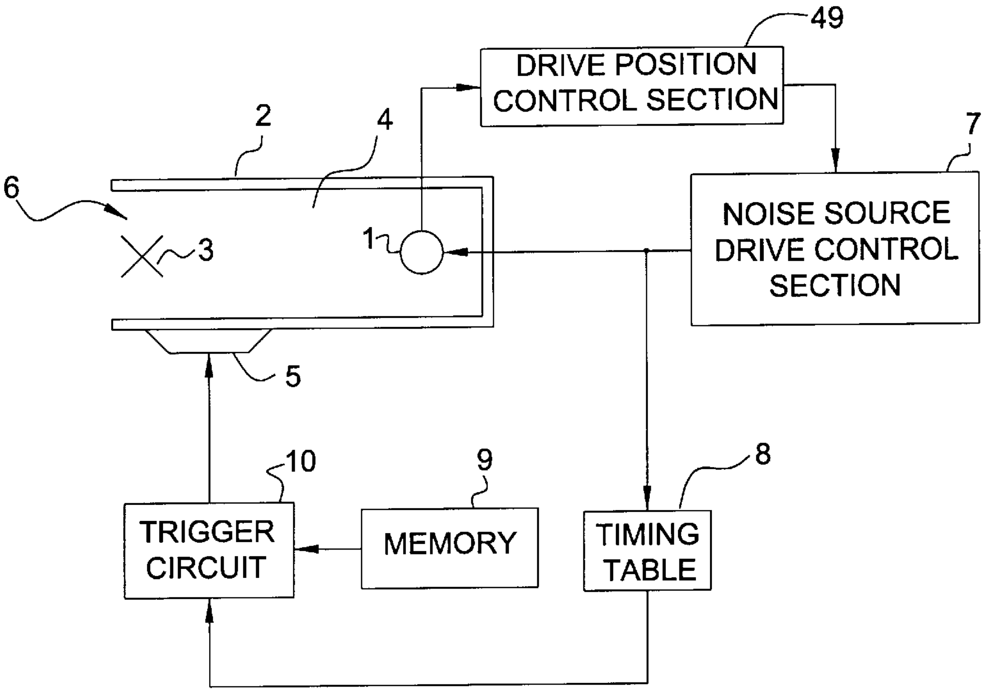
FIG. 10 is a block diagram of assistance in explaining the construction of a noise suppressor in an image forming apparatus according to a fourth embodiment of the present invention.

FIG. 10 is a block diagram of assistance in explaining the construction of a noise suppressor in an image forming apparatus according to a fourth embodiment of the present invention. In FIG. 10, reference numeral 1 designates a noise source of the drive mechanism of the image forming apparatus; 2, a duct which is a passage for sound; 3, a noise suppressing point; 4, a space of the duct; 5, a secondary sound source speaker generating a control sound (a secondary sound) for suppressing the noise; 6, a duct opening; 7, a noise source drive control section; 8, a timing table; 9, a memory for storing reversed waveform information for suppressing the noise in response to the drive mechanism (noise source); and 10, a trigger circuit for reading a designated timing of the reversed waveform from the memory. These are the same as those described in the first embodiment. Reference numeral 49 designates a drive position control section for setting an initial position of the drive mechanism as the noise source.

In the fourth embodiment, the drive position control section 49 is provided in addition to the construction of the first embodiment (FIG. 1). This drive position control section 49 sets the initial position to a fixed position in the case where the drive mechanism of the noise source 1 starts its operation. For example, an example will be described in detail in which the drive mechanism of the noise source 1 is a drive motor for a rotary polygon mirror in an optical scanning system of a copying machine. In this case, for example, a drive motor 40 for a rotary polygon mirror 42 is provided with position sensors (43, 45–47) for determining a rotary position, as shown in FIGS. 11 to 13, in order to detect a fixed initial position of the drive motor for the rotary polygon mirror.

Figure 11:
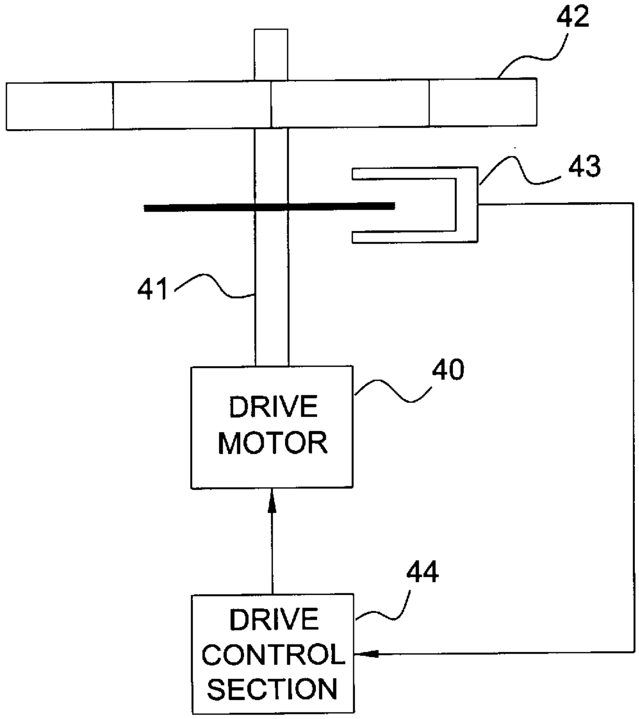
FIG. 11 is a view of assistance in explaining one example of the drive start position control in a drive mechanism.

FIG. 11 is a view of assistance in explaining one example of the drive start position control in a drive mechanism. As shown in FIG. 11, the rotary polygon mirror 42 used in the optical scanning system for forming one recording image of the drive mechanism of the copying machine is mounted integrally with a drive shaft 41 of the drive motor 40 and rotates as the drive motor 40 rotates. Because of this, noises such as an air sound caused by the rotary polygon mirror 42, an electromagnetic sound of the drive motor 40 and the like are generated to comprise violent noises. The phase of these noises is different with the rotation start position of the drive motor 40. Therefore, in the noise depressor in the fourth embodiment, the drive start position is set so as to start at a fixed position always. With this, the phase of the signal of fixed inverted waveform information of the reversed waveform information stored in advance in the memory 9 is always matched to effectively relieve the noise.

Therefore, in the noise suppressor in the fourth embodiment, in order that each of the drive mechanisms always starts from a fixed position, for example, as shown in FIG. 11, a rotary plate of an encoder as a position sensor is mounted integrally with the rotary shaft 41. Information from a read portion 43 of the encoder is fed to the drive control section 44, and when the drive motor 40 stops, it always stops at a fixed rotary position of the drive motor 40. As a result, the next drive is always started at the same position.

Figure 12:
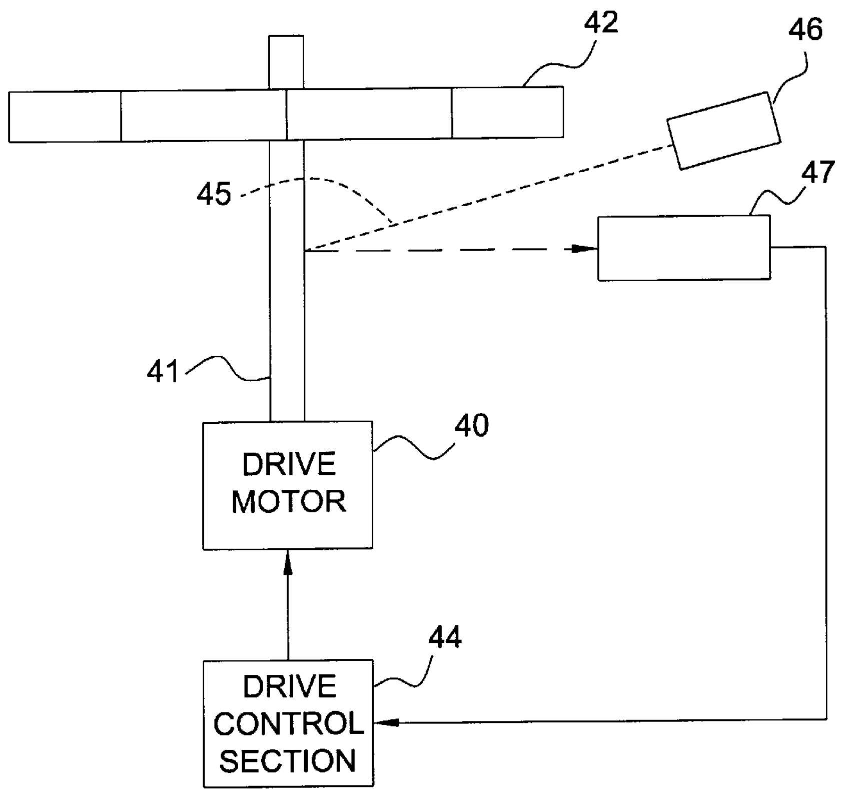
FIG. 12 is likewise a view of assistance in explaining a further example of the drive start position control.
Figure 13:
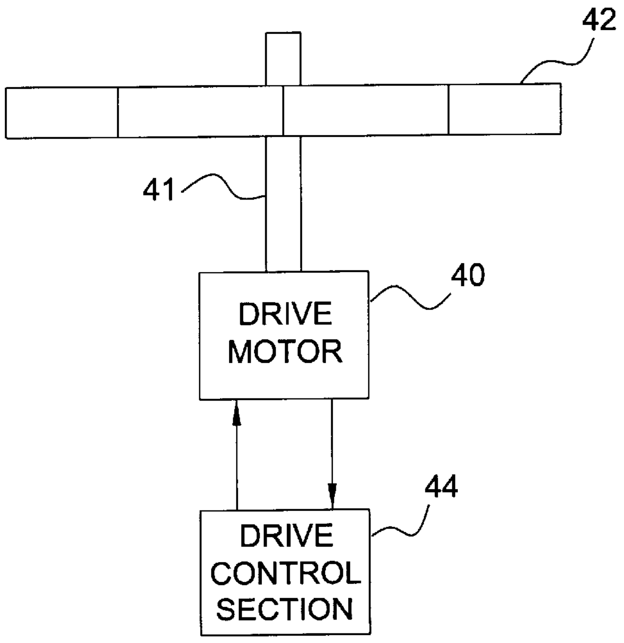
FIG. 13 is likewise a view of assistance in explaining another example of the drive start position control.
Figure 14:
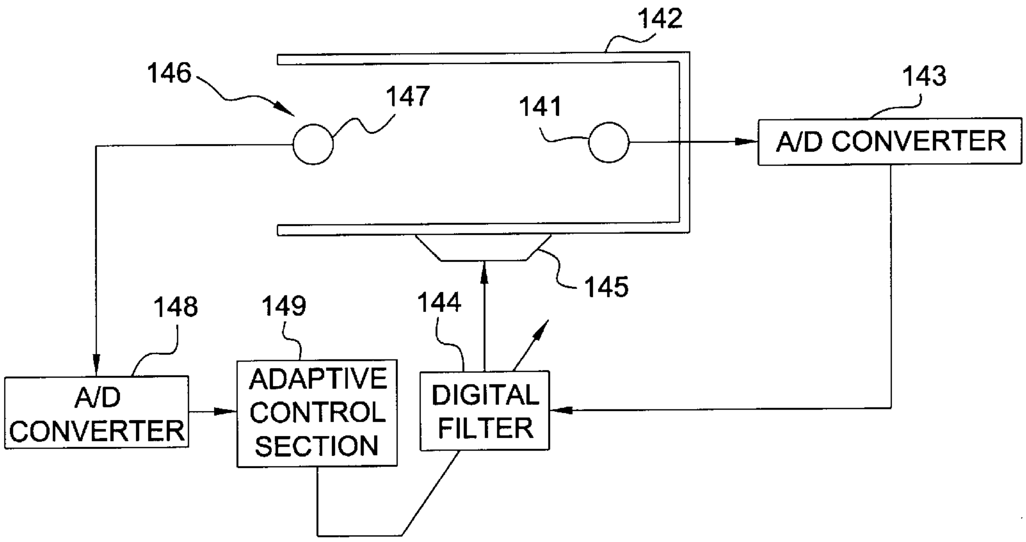
FIG. 14 is a view of assistance in explaining the construction of a noise suppressing system in prior art.
Figure 15:
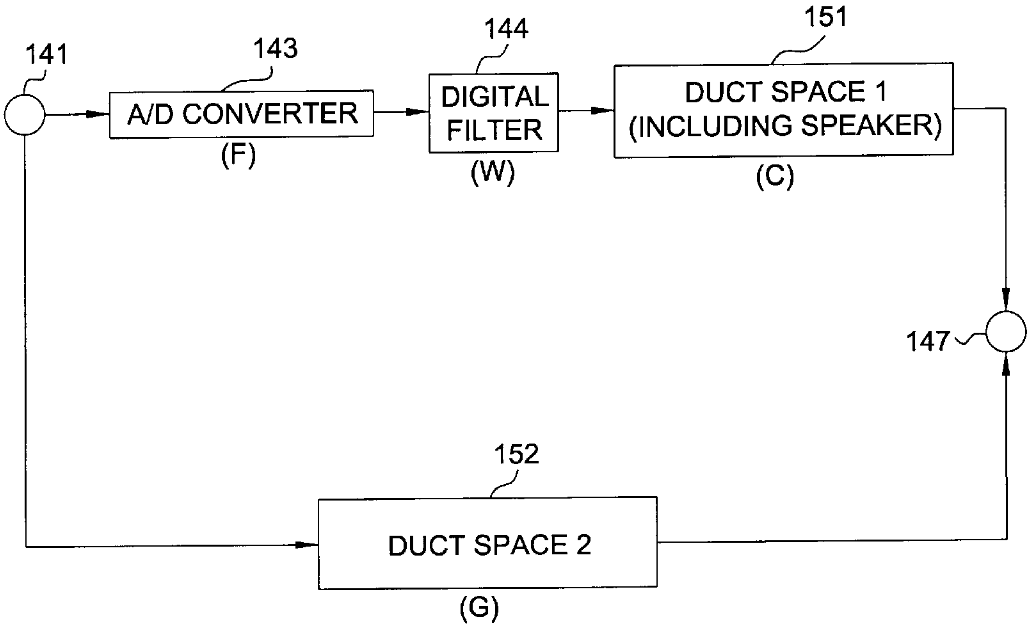
FIG. 15 is a signal block diagram of a conventional noise suppressing system.

FIG. 12 is likewise a view of assistance in explaining a further example of the drive start position control. FIG. 12 shows an example in which a reflection mark 45 is provided at a part of the rotary shaft 41 of the drive motor 40 on which the rotary polygon mirror 42 is integrally mounted, as a position sensor. In the example of the drive start position control shown in FIG. 12, a laser beam from a laser source 46 is irregularly reflected. The laser beam is not received at a light receiver 47 but the laser beam is reflected at the reflection mark 45 and the laser beam is detected at the light receiver 47. Thus, the reflected light is detected to perform the drive start position control. That is, it is so controlled that when the drive motor 40 stops, the drive motor 40 stops at a position where the laser beam is detected by a signal from the light receiver 47.

FIG. 13 is likewise a view of assistance in explaining another example of the drive start position control. As shown in FIG. 13, a Z-phase of the drive motor 40 is detected without provision of a special position sensor on the rotary shaft 41 of the drive motor 40 on which the rotary polygon mirror 40 is integrally mounted so that stopping of the drive motor 40 is always effected at the Z-phase. In the method for detecting the Z-phase, since a position sensor need not be specially provided, the method can be applied without modification to a drive motor of a general rotary system such as an exhaust fan.

The operation of the noise suppressor in the fourth embodiment will be briefly described with reference to FIG. 10. In the noise suppressor in the fourth embodiment, there is provided a drive position control section 49 for always controlling the drive start position of the drive mechanism to a fixed position. The noise sound drive control section 7 is controlled by the drive position control section 49 prior to the normal copying operation to set the drive start position of the drive source 1 to a fixed position, after which the operation of the drive mechanism as the noise source 1 (copying operation) is started. As previously explained in the first embodiment, the drive timing of the noise source 1 and the reading timing from the memory 9 are stored in the timing table 8, and the trigger circuit 10 for reading reversed waveform information from the memory 9 is actuated in response to the drive order signal output from the noise source drive control section 7 with respect to the noise source 1.

By the operation of the trigger circuit 10, the signal of the reversed waveform of the noise caused by the reversed waveform information read from the memory 9 is fed to the secondary sound source speaker 5 and reproduced, and at the noise suppressing point 3, the noise from the noise source 1 is suppressed by the reversed waveform so that two sounds interfere and offset each other thus suppressing the noise.

As described above, according to the noise suppressor in the image forming apparatus of the present invention, since noises of various noise sources (drive mechanisms) can be suppressed at a small and inexpensive system, it is possible to suppress the noise effectively without bringing a larger size or an increase in cost of a small and inexpensive laser beam printer, a copying machine and the like. Further, it is possible to easily suppress shock sounds which could not be handled by the control of a conventional noise suppressing system, and a great effect can be obtained with respect to the reduction in noises of a copying machine which involves much shock sounds.

What is claimed is:

1. A noise suppressor in an image forming apparatus having a drive mechanism, comprising:
 - operation timing information memory means for storing operation timing information of said drive mechanism in a timing table,
 - signal detection means for detecting an operation start signal of said drive mechanism,
 - a speaker for generating a secondary sound having a waveform of the same amplitude as and opposite phase from a waveform of a noise generated by said drive mechanism, and
 - speaker control means for generating the secondary sound from said speaker on the basis of a detection signal from said signal detection means and the operation timing information from the timing table, said speaker control means comprising waveform information memory means for storing at least waveform information having a waveform reversed to said waveform of said noise generated by said drive mechanism, and trigger means for reading the waveform information stored in said waveform information memory means based on the operation timing information stored in the timing table.

2. The noise suppressor in an image forming apparatus according to claim 1, further comprising initial state setting means for setting an operation start position of said drive mechanism to an initial state.

3. The noise suppressor in an image forming apparatus according to claim 2, wherein said drive mechanism includes a drive motor, and said initial state setting means is setting means for setting said drive motor so that the latter stops at a fixed rotational position.

4. A noise suppressor in an image forming apparatus having a drive mechanism, comprising:
 - operation timing information memory means for storing operation timing information of said drive mechanism in an operating mode of said image forming apparatus in a timing table,
 - discrimination means for discriminating the operating mode of said image forming apparatus,
 - timing reading means for reading operation timing information of said drive mechanism corresponding to the operating mode discriminated by said discrimination means,
 - a speaker for generating a secondary sound having a waveform of the same amplitude as and opposite phase from a waveform of a noise generated by said drive mechanism, and
 - speaker control means for generating the secondary sound from said speaker on the basis of the operation timing information read by said timing reading means, said speaker control means comprising waveform information memory means for storing at least waveform information having a waveform reversed to said waveform of said noise generated by said drive mechanism, and trigger means for reading the waveform information stored in said waveform information memory means based on the operation timing information stored in the timing table.

5. The noise suppressor in an image forming apparatus according to claim 4, further comprising: initial state setting means for setting an operation start position of said drive mechanism to an initial state.

6. The noise suppressor in an image forming apparatus according to claim 5, wherein said drive mechanism includes a drive motor and said initial state setting means is setting means for setting said drive motor so that the latter stops at a fixed rotational position.

7. A noise suppressing method in an image forming apparatus having a drive mechanism, comprising:
 - storing operation timing information of said drive mechanism in a timing table,
 - detecting an operation start signal of said drive mechanism,
 - generating a previously stored secondary sound having a waveform of the same amplitude as and opposite phase from a waveform of a noise generated by said drive mechanism,
 - triggering the generation of the previously stored secondary sound on the basis of said operation start signal and said operation timing information from the timing table, and interfering with the noise generated by said drive mechanism with said previously stored secondary sound to suppress said noise at a noise suppressing position.

8. The noise suppressing method in an image forming apparatus according to claim 7, further comprising: setting the operation start position of said drive mechanism to an initial state before the operation of said drive mechanism starts.

9. The noise suppressing method in an image forming apparatus according to claim 7, further comprising: measuring the transmission characteristics of said previously stored secondary sound from an installation position of said speaker to said noise suppressing position, and changing a phase of said previously stored secondary sound on the basis of said measured result.

10. The noise suppressing method in an image forming apparatus according to claim 7, further comprising: measuring the transmission characteristics of said previously stored secondary sound from an installation position of said speaker to said noise suppressing position, and changing an amplitude of said previously stored secondary sound on the basis of said measured result.

11. A noise suppressing method in an image forming apparatus having a drive mechanism, comprising:

storing in a timing table operation timing information of said drive mechanism in an operating mode for forming an image, discriminating the operating mode for forming an image by a start of said image formation, reading the operation timing information of said drive mechanism corresponding to the discriminated operating mode, generating a previously stored secondary sound having a waveform of the same amplitude as and opposite phase from a waveform of a noise generated from said drive mechanism, triggering the generation of the previously stored secondary sound on the basis of said read operation timing information, and interfering with the noise generated from said drive mechanism with said previously stored secondary sound to suppress said noise at a noise suppressing position.

12. The noise suppressing method in an image forming apparatus according to claim 11, further comprising: setting an operation start position of said drive mechanism to an initial state before operation of said drive mechanism starts.

13. The noise suppressing method in an image forming apparatus according to claim 11, further comprising: measuring transmission characteristics of said previously stored secondary sound from an installation position of said speaker to said noise suppressing position, and changing a phase of said previously stored secondary sound on the basis of said measured result.

14. The noise suppressing method in an image forming apparatus according to claim 11, further comprising: measuring transmission characteristics of said previously stored secondary sound from an installation position of said speaker to said noise suppressing position, and changing an amplitude of said previously stored secondary sound on the basis of said measured result.

* * * * *